US010883079B2

(12) United States Patent
Wang et al.

(10) Patent No.: US 10,883,079 B2
(45) Date of Patent: Jan. 5, 2021

(54) METHOD FOR PREPARING MICROENCAPSULATED HEAT-SENSITIVE BIOACTIVE MATERIAL

(71) Applicant: HER MAJESTY THE QUEEN IN RIGHT OF CANADA, AS REPRESENTED BY THE MINISTER OF AGRICULTURE AND AGRI-FOOD, Guelph (CA)

(72) Inventors: Qi Wang, Guelph (CA); Huan Liu, Guelph (CA); Jianhua Gong, Guelph (CA); Hai Yu, Guelph (CA); Qian Guo, Guelph (CA); Shea Miller, Ottawa (CA); Wuwei Cui, Guelph (CA)

(73) Assignee: HER MAJESTY THE QUEEN IN RIGHT OF CANADA, AS REPRESENTED BY THE MINISTER OF AGRICULTURE AND AGRI-FOOD, Guelph (CA)

( * ) Notice: Subject to any disclaimer, the term of this patent is extended or adjusted under 35 U.S.C. 154(b) by 0 days.

(21) Appl. No.: 15/565,558

(22) PCT Filed: Mar. 24, 2016

(86) PCT No.: PCT/CA2016/050344
§ 371 (c)(1),
(2) Date: Oct. 10, 2017

(87) PCT Pub. No.: WO2016/161506
PCT Pub. Date: Oct. 13, 2016

(65) Prior Publication Data

US 2018/0119088 A1 May 3, 2018

Related U.S. Application Data

(60) Provisional application No. 62/144,137, filed on Apr. 7, 2015.

(51) Int. Cl.

| | |
|---|---|
| ***C12N 1/04*** | (2006.01) |
| ***A23K 40/30*** | (2016.01) |
| ***A23P 10/30*** | (2016.01) |
| ***A23P 10/35*** | (2016.01) |
| ***A23L 33/135*** | (2016.01) |
| ***A23D 7/05*** | (2006.01) |
| ***A61K 35/747*** | (2015.01) |
| ***A61K 9/16*** | (2006.01) |
| ***A61K 47/42*** | (2017.01) |
| ***B01J 13/04*** | (2006.01) |
| ***C12N 11/04*** | (2006.01) |
| ***A23D 7/005*** | (2006.01) |
| ***A23D 9/05*** | (2006.01) |

(52) U.S. Cl.
CPC ............. *C12N 1/04* (2013.01); *A23D 7/0053* (2013.01); *A23D 7/05* (2013.01); *A23D 9/05* (2013.01); *A23K 40/30* (2016.05); *A23L 33/135* (2016.08); *A23P 10/30* (2016.08); *A23P 10/35* (2016.08); *A61K 9/1652* (2013.01); *A61K 35/747* (2013.01); *A61K 47/42* (2013.01); *B01J 13/043* (2013.01); *C12N 11/04* (2013.01); *A23V 2002/00* (2013.01)

(58) Field of Classification Search
None
See application file for complete search history.

(56) References Cited

U.S. PATENT DOCUMENTS

| | | | | |
|---|---|---|---|---|
| 5,292,657 | A | 3/1994 | Rutherford et al. | |
| 8,337,923 | B2 * | 12/2012 | Coyne ...................... | A21D 2/00 426/326 |
| 8,871,266 | B2 | 10/2014 | Crittenden et al. | |
| 2008/0044481 | A1 | 2/2008 | Harel | |
| 2009/0238885 | A1 | 9/2009 | Alting et al. | |
| 2010/0297222 | A1 | 11/2010 | Kanaya et al. | |
| 2011/0008493 | A1 | 1/2011 | Zorea | |
| 2012/0189735 | A1 | 7/2012 | Wright et al. | |
| 2014/0093614 | A1 | 4/2014 | Gonzalez et al. | |

FOREIGN PATENT DOCUMENTS

| | | | | |
|---|---|---|---|---|
| CA | 2529479 | A1 | 12/2004 | |
| WO | WO-2005030229 | A1 * | 4/2005 | .............. A61K 9/19 |
| WO | 2012077038 | A1 | 6/2012 | |

OTHER PUBLICATIONS

Babiker et al. Nutr J. 2012; 11:111.*
Liu et al. Journal of Food Quality 34 (2011) 64-73.*
Wolfe, Lindsay Ann. Encapsulation of Probiotic Bacteria in a Water in Solid Fat Emulsion to Promote Acid resistance. Master of Science Thesis. The Pennsylvania State University. Dec. 2012.*
Chavarri, Maria, et al., "Encapsulation Technology to Protect Probiotic Bacteria." Probiotics, Prof. Everlon Rigobelo (Ed.), InTech, 2012, DOI: 10.5772/50046. Available from: https://www.intechopen.com/books/probiotics/encapsulation-technology-to-protect-probiotic-bacteria.

(Continued)

*Primary Examiner* — Oluwatosin A Ogunbiyi
(74) *Attorney, Agent, or Firm* — Saliwanchik, Lloyd & Eisenschenk

(57) ABSTRACT

Microparticles include a matrix of an encapsulating material, in which are dispersed particles of a low melting point fat and a bioactive material, such as one or more probiotic bacteria. The microparticles are formed by preparing an emulsion of melted low melting point fat in an aqueous mixture of the encapsulating material, cooling the emulsion below the melting point of the low melting point fat, dispersing the bioactive material in the emulsion and spray drying the emulsion. The particles of solid low melting point fat are believed to protect the bioactive material from heat damage during the spray drying process.

14 Claims, 11 Drawing Sheets

(56) References Cited

OTHER PUBLICATIONS

Favaro-Trindade, C.S., et al., "Developments in probiotic encapsulation.", CAB Reviews: Perspectives in Agriculture, Veterinary Science, Nutrition and Natural Resources, 2011, 6(004): 1-8.

Liu, Huan, et al., "Protection of heat-sensitive probiotic bacteria during spray-drying by sodium caseinate stabilized fat particles." Food Hydrocolloids, 2015, 51: 459-467.

Liu, Huan, et al., "Incorporation of polysaccharides into sodium caseinate-low melting point fat microparticles improves probiotic bacterial survival during simulated gastrointestinal digestion and storage." Food Hydrocolloids, 2016, 54: 328-337.

Pedroso, D.L., et al., "Microencapsulation of Bifidobacterium animalis subsp. *lactis* and *Lactobacillus acidophilus* in cocoa butter using spray chilling technology." Brazilian Journal of Microbiology, 2013, 44(3): 777-783.

Würth, R., et al., "Protective effect of milk protein based microencapsulation on bacterial survival in simulated gastric juice versus the murine gastrointestinal system." Journal of Functional Foods, 2015, 15: 116-125.

* cited by examiner

METHOD FOR PREPARING MICROENCAPSULATED HEAT-SENSITIVE BIOACTIVE MATERIAL

CROSS REFERENCE TO A RELATED APPLICATION

This application is a National Stage Application of International Application Number PCT/CA2016/050344, filed Mar. 24, 2016; which claims the benefit of U.S. Provisional Application Ser. No. 62/144,137, filed Apr. 7, 2015; both of which are incorporated herein by reference in their entirety.

BACKGROUND

The present invention relates to microencapsulation methods for bioactive materials. More specifically, the present invention relates to microparticles containing probiotic bacteria or other heat-sensitive bioactive materials, and to methods of preparing the microparticles.

Many bioactive materials, including probiotic bacteria, can be beneficial to human and animal health when ingested, for example, as supplements or additives to food products or animal feed. However, such materials are sensitive to the adverse environmental conditions encountered when ingested, such as the acidic conditions found within the stomach, or high bile salt concentrations found in the upper intestine. Thus, these materials may undergo significant loss of viability or functionality before they reach their target site within the body. Encapsulating such materials can provide protection against such adverse environmental conditions, thereby improving viability. International Patent Application WO 2012/077038, U.S. Pat. No. 8,871,266 and US Patent Application Publications 2012/0189735, 2011/0008493 and 2009/0238885 describe encapsulation of bioactive materials.

However, bioactive materials can also undergo environmental challenges during the encapsulation process. For example, spray drying is a well-established technique for encapsulating food and feed ingredients. Spray drying is a continuous and rapid process with low cost and high reproducibility, and thus is highly suitable for large-scale, industrial applications. However, conventional spray drying procedures expose bioactive material, such as probiotic bacterial cells, to adverse conditions, including high temperature, which can reduce their viability. During spray drying, bacterial cells experience heat stress, dehydration, oxygen exposure and osmotic stress, which could lead to the loss of metabolic activity and even death of the cells. Attempts to address such challenges include the selection of thermal resistant bacterial strains, heat treatment of bacteria prior to spray drying, and the use of prebiotics or thermoprotectants such as granular starch, soluble fiber and trehalose. However, these methods can be difficult and time consuming and are not always successful.

Therefore, there is a need in the industry for an alternative method to protect probiotic bacterial cells and other heat-sensitive bioactive material from damage due to heat exposure during processing, including encapsulation procedures involving spray drying. Such a method may make it possible to use spray drying techniques to conveniently encapsulate heat-sensitive bioactive materials for which previously known spray drying processes are not suitable or effective.

SUMMARY

One aspect of the present invention provides microparticles including a matrix of an encapsulating material, in which are dispersed smaller particles of a low melting point fat and a bioactive material. The particles of the low melting point fat are substantially separate and distinct from the bioactive material.

In another aspect, the present invention provides a method of preparing microparticles, the method including heating a low melting point fat to form a liquid melt; mixing the liquid melt with an aqueous mixture of an encapsulating material to form an emulsion; cooling the emulsion below the melting point of the low melting point fat; dispersing a bioactive material into the emulsion; and spray drying the emulsion to form the microparticles.

In at least one embodiment, the encapsulating material comprises sodium caseinate. In at least one embodiment, the encapsulating material further comprises gum arabic. In at least one embodiment, the low melting point fat has a melting point of greater than about 25° C. In at least one embodiment, the low melting point fat has a melting point of about 25° C. to about 60° C. In at least one embodiment, the low melting point fat is selected from shortenings, cocoa butter, margarine, fatty acids, lard, suet, palm oil, fractionated palm oil, hydrogenated oils and mixtures thereof. In at least one embodiment, the low melting point fat is selected from palm oil, hydrogenated cottonseed oil and mixtures thereof. In at least one embodiment, the bioactive material comprises one or more probiotic bacteria. In at least one embodiment, the one or more probiotic bacteria comprise one or more *Lactobacillus* species.

BRIEF DESCRIPTION OF THE DRAWINGS

Further features of the present invention will become apparent from the following written description and the accompanying figures, in which.

DETAILED DESCRIPTION

Figure 1:
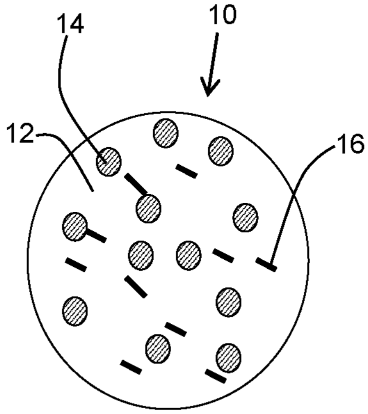
FIG. 1 is a diagram of a spray-dried microparticle according to an embodiment of the invention including low melting point fat particles and probiotic bacteria.

One aspect of the present invention provides microparticles. With reference to FIG. 1, spray dried microparticles 10 include a matrix 12 of an encapsulating material, dispersed in which are smaller particles of a low melting point fat 14 and a bioactive material 16. The particles of the low melting point fat are substantially separate and distinct from the bioactive material. As used herein, the term "microparticle" is intended to mean a particle which has a diameter of from about 0.1 μm to about 100 μm.

As used herein, the term "about" or "approximately" as applied to a numerical value or range of values is intended to mean that the recited values can vary within an acceptable degree of error for the quantity measured given the nature or precision of the measurements, such that the variation is considered in the art as equivalent to the recited values and provides the same function or result. For example, the degree of error can be indicated by the number of significant figures provided for the measurement, as is understood in the art, and includes but is not limited to a variation of ±1 in the most precise significant figure reported for the measurement. Typical exemplary degrees of error are within 20 percent (%), preferably within 10%, and more preferably within 5% of a given value or range of values. Alternatively, and particularly in biological systems, the terms "about" and "approximately" can mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

As used herein, the term "substantially" refers to the complete or nearly complete extent or degree of an action, characteristic, property, state, structure, item, or result. For example, a particle that is "substantially" separate from another particle within a matrix is intended to mean that the particles are either completely separated by intervening matrix material or nearly completely separated so that some incidental contact is possible, but the particles do not undergo any degree of contact or intermixing which would have a measureable effect on their individual functions or structures. The exact allowable degree of deviation from absolute completeness may in some cases depend on the specific context. However, generally speaking the nearness of completion will be so as to have the same overall result as if absolute and total completion were obtained.

The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of"

an ingredient or element may still actually contain such item as long as there is no measurable effect thereof.

As used herein, the term "bioactive material" is intended to mean microorganisms, material derived from or produced by organisms or microorganisms (including but not limited to tissue, genetic material, extracts, products including but not limited to enzymes, and the like), or organic material which has biological activity or which is necessary or desirable to sustain life functions (including but not limited to drugs, food and organic nutrients including but not limited to proteins, carbohydrates, vitamins, and the like). As used herein, the term "microorganisms" is intended to mean unicellular, multicellular or non-cellular microscopic organisms and includes but is not limited to prokaryotic microorganisms including but not limited to bacteria, archaea and the like; eukaryotic microorganisms including but not limited to algae, protists, fungi, yeasts, molds, mites, nematodes and the like; and infectious particles including but not limited to viruses, phages, prions and the like. Bioactive material can be, but need not necessarily be, alive.

In at least one embodiment, the bioactive material is a heat-sensitive bioactive material whose viability can be reduced if the bioactive material is exposed to temperatures above a predefined range. As used herein, the term "viability" is intended to mean the ability to live or be sustained, or to fulfil a biological function. Conditions under which a bioactive material is viable need not be those under which the bioactive material is actively growing or functioning, but can also include conditions under which the bioactive material is inactive or dormant, as long as it retains at least some potential to live or fulfil its function. Non-living bioactive material can have viability if it has not decomposed or been deactivated beyond its ability to fulfil its intended biological function.

It will be understood by the skilled person that different bioactive materials have different optimal temperature ranges at which viability can be maintained or preserved. Therefore some bioactive materials are readily damaged or destroyed, so as to lose or experience reduced viability, by exposure to temperatures at which other bioactive materials will retain full or significant viability. For example, damage can occur at various sites in bacterial cells including the cell wall, cytoplasmic membrane, ribosomes, RNA and DNA. However, there is often a critical temperature above which the survival of cells decreases dramatically, and this critical temperature can be different for different microorganisms, including but not limited to different species, strains, varieties or isolates. At temperatures below the critical temperature, the cell membrane is likely to be the main site at which damage occurs, while at temperatures above the critical temperature, denaturation of ribosomes and/or proteins, as well as damage to the cell wall can occur and lead to thermal death of the cells.

The present microparticles include a matrix of an encapsulating material. Suitable encapsulating materials are well known in the art and include, but are not limited to, proteins such as casein or sodium caseinate, whey protein, soy protein, gelatin and the like, carbohydrates such as gum arabic, carrageenan, locust bean gum, gellan gum, xanthan gum, cellulose acetate phthalate, starch, pectin, alginate, chitosan and the like, and mixtures thereof.

The present microparticles include particles of a low melting point fat dispersed in the matrix of the encapsulating material. In at least one embodiment, the low melting point fat will have a melting point above normal room temperature, so as to be in the solid phase under normal ambient conditions. Thus, a low melting point fat would not include an oil which is normally liquid under normal ambient conditions, as understood in the art. In at least one embodiment, the low melting point fat will have a melting point above about 25° C. In at least one embodiment, the low melting point fat will have a melting point in the range of about 25° C. to about 60° C. In at least one embodiment, the low melting point fat will have a melting point in the range of about 25° C. to about 45° C. In at least one embodiment, the low melting point fat will have a melting point in the range of about 30° C. to about 45° C. Suitable low melting point fats are known and include but are not limited to shortenings, cocoa butter, margarine, fatty acids, lard, suet, palm oil, fractionated palm oil, hydrogenated oils and mixtures thereof. Hydrogenated oils include but are not limited to hydrogenated palm oil, hydrogenated cottonseed oil and hydrogenated coconut oil. In at least one embodiment, the low melting point fat is selected from palm oil, hydrogenated cottonseed oil and mixtures thereof.

In at least one embodiment, the ratio of low melting point fat to encapsulating material in the microparticles varies from about 0.25:1 to about 1:1 by weight. In at least one embodiment, the ratio of low melting point fat to encapsulating material in the microparticles varies from about 0.50:1 to about 1:1 by weight. In at least one embodiment, the ratio of low melting point fat to encapsulating material in the microparticles varies from about 0.75:1 to about 1:1 by weight. In at least one embodiment, the ratio of low melting point fat to encapsulating material in the microparticles is about 1:1 by weight.

In at least one embodiment, the present microparticles are prepared by heating the low melting point fat to form a liquid melt; mixing the liquid melt with an aqueous mixture of an encapsulating material to form an emulsion; cooling the emulsion below the melting point of the low melting point fat to allow solidification of the fat particles, dispersing the bioactive material into the emulsion; and spray drying the emulsion to form the microparticles.

The low melting point fat can be melted to form the liquid melt at any temperature above its melting point which will maintain the low melting point fat in liquid form without causing measurable or detrimental decomposition. Once melted, the liquid melt can be mixed with an aqueous mixture of an encapsulating material at a temperature at which the low melting point fat would remain melted, so as to form an emulsion. The emulsion can be prepared by using techniques well known in the art, including but not limited to blending and/or homogenizing the mixture of the liquid melt and the aqueous mixture of the encapsulating material, and treating the mixture of the liquid melt and the aqueous mixture of the encapsulating material with ultrasound.

In at least one embodiment, the aqueous mixture of the encapsulating material is an aqueous solution of the encapsulating materials described herein above. In at least one embodiment, the aqueous mixture further comprises one or more additives, including but not limited to prebiotics and protectants and antioxidants. Suitable prebiotics and protectants include but are not limited to sugars, oligosaccharides and polysaccharides, including but not limited to starch, maltodextrin, inulin, trehalose, and the like. Suitable antioxidants are advantageously lipid-soluble antioxidants, including but not limited to butylated hydroxyanisole (BHA), butylated hydroxytoluene (BHT), tert-butylhydroquinone (TBHQ), vitamin E, tocopherols, tocotrienols, and the like.

In at least one embodiment, the prepared emulsion of the low melting point fat and the aqueous mixture of the encapsulating material is cooled below the melting point of the low melting point fat, such that solid particles of the low melting point fat are formed, and the bioactive material is dispersed in the emulsion. The bioactive material can be added to the emulsion in any convenient form, including but not limited to a solution or dispersion in a suitable solvent, such as water. If the bioactive material includes one or more microorganisms, it can be added as a suspension in a culture medium or diluted culture medium. The bioactive material can be dispersed in the emulsion by any known technique, including but not limited to stirring and vibration.

The emulsion containing the dispersed bioactive material is then spray dried, using apparatus and conditions well known in the art, to form the encapsulated bioactive material in the form of a powder. Advantageously, the outlet temperature of the spray drying apparatus is as high as possible without causing deleterious effect to the bioactive material, as will be understood in the art. Without being bound by theory, it is believed that higher outlet temperatures, where possible without deleterious effect, will advantageously reduce the water content of the spray dried powder and improve the storage stability of the spray dried powder. In at least one embodiment, the spray drying can be carried out at an outlet temperature of from about 65° C. to about 80° C. However, the skilled person is readily able to select other suitable outlet temperatures for various bioactive materials in light of the teaching herein.

Without being bound by theory, it is believed that the droplets of low melting point fat dispersed through the emulsion return to the solid crystal phase when the emulsion is cooled below the melting point of the low melting point fat. After the emulsion containing the bioactive material is transferred into the spray drier, it first passes for a short period through a chamber in which the temperature is almost as high as the inlet temperature. The emulsion is then sprayed through a nozzle as micro-droplets into the drying chamber. The encapsulated bioactive material can be exposed to high temperatures in these locations. At such temperatures, the low melting point fat particles can melt or undergo a solid to liquid phase transition, thereby absorbing heat while maintaining a constant temperature. Because of this heat absorption, the temperature of any bioactive material embedded in the encapsulating material in the vicinity of the melting fat particles is prevented from increasing to the extent that it would if the fat particles were not present. Thus, in at least one embodiment of the present microparticles, the particles of low melting point fat within the matrix of encapsulating material can protect the encapsulated bioactive material, including but not limited to probiotic bacteria, from heat damage during the spray drying process. Furthermore, in at least one embodiment of the present microparticles, it is contemplated that the particles of low melting point fat within the matrix of encapsulating material can protect the encapsulated bioactive material, including but not limited to probiotic bacteria, from heat damage during other processing steps involving heat.

EXAMPLES

Other features of the present invention will become apparent from the following non-limiting examples which illustrate, by way of example, the principles of the invention.

Sodium caseinate (NaCas) was purchased from Sigma-Aldrich Chemical Co., Ltd (St. Louis, Mo., USA). Vegetable oil and low melting point fat (LMF) were obtained from UNICO Inc. (ON, Canada) and 101 Loders Croklaan Inc. (Sanslrans™ 39, IL, USA), respectively. Glassware was sterilized at 121° C. for 15 min. The stains 4',6-diamidino-2-phenylindole (DAPI) and fluorescein isothiocyanate (FITC) were purchased from Sigma-Aldrich (St-Louis, Mo., USA), and 9-diethylamino-5H-benzo[α]phenoxazine-5-one (Nile Red) was purchased from Kodak (Rochester, N.Y., USA).

The results of each data point in the graphs shown in the Figures represent the mean of triplicate experiments and the error bars indicate the standard deviations for the data points. All differences were considered statistically significant at a 0.05.

Example 1

Preparation of *Lactobacillus* Isolates

*Lactobacillus zeae* LB1 (LB1) and *Lactobacillus reuteri* S64 (S64) and K67 (K67) are isolates from chicken or pig intestines with the capacity to inhibit *Salmonella* or *E. coli* infection in *Caenorhabditis elegans*, broiler chickens, or pigs. Isolates from stock cultures in 15% (v/v) aqueous glycerol at −80° C. were cultured on de Man, Rogosa and Sharpe (MRS) agar (BD Institution, MD, USA) for recovery and single colony purification. Each isolate was sub-cultured twice in MRS broth at 37° C. for 24 h prior to preparation of a fresh culture inoculated (1%, v/v) in MRS broth and grown at 37° C. for 12 hours. All cultures were grown under anaerobic atmosphere (80% $N_2$, 15% $CO_2$ and 5% $H_2$) and were harvested in the early stationary phase. A probiotic culture in the stationary phase often has better heat resistance than in the exponential phase. Bacterial cells were harvested by centrifugation (Sorvall™ RC 6 Plus, Thermo Scientific Inc., MA, USA) at 4,000× g for 20 min (4° C.) and washed twice with sterile 0.85% (w/v) sodium chloride solution. The pellet was then re-suspended in sterile 0.85% (w/v) sodium chloride solution to obtain a suspension containing approximately $10^{10}$ colony-forming units (CFU)/mL. The bacterial suspension ($10^{10}$ CFU/mL) was stored at 4° C. and used on the same day.

Example 2

Thermal Tolerance of *Lactobacillus* Isolates

Two 50 mL bottles containing 19 mL NaCas solution (10%, w/w) were placed in a water bath at test temperatures of 54° C., 57° C., 60° C., 63° C. and 66° C. One of the bottles was a control used to monitor the temperature. When the desired temperature was reached, 1 mL of either *Lactobacillus zeae* LB1 (LB1) or *Lactobacillus reuteri* S64 (S64) or K67 (K67) cell suspension (Example 1) was added to the second bottle. At selected intervals (between 30 s and 5 min), 1 mL aliquots were removed from the test bottle, serially diluted in MRS broth and plated on MRS agar for CFU counts. Enumeration was performed after 24 h of anaerobic incubation at 37° C. The plating and enumeration were accomplished using an Eddy Jet Spiral Plater (Neu-tec Group, Farmingdale, N.Y., USA).

Results

Figure 3A:
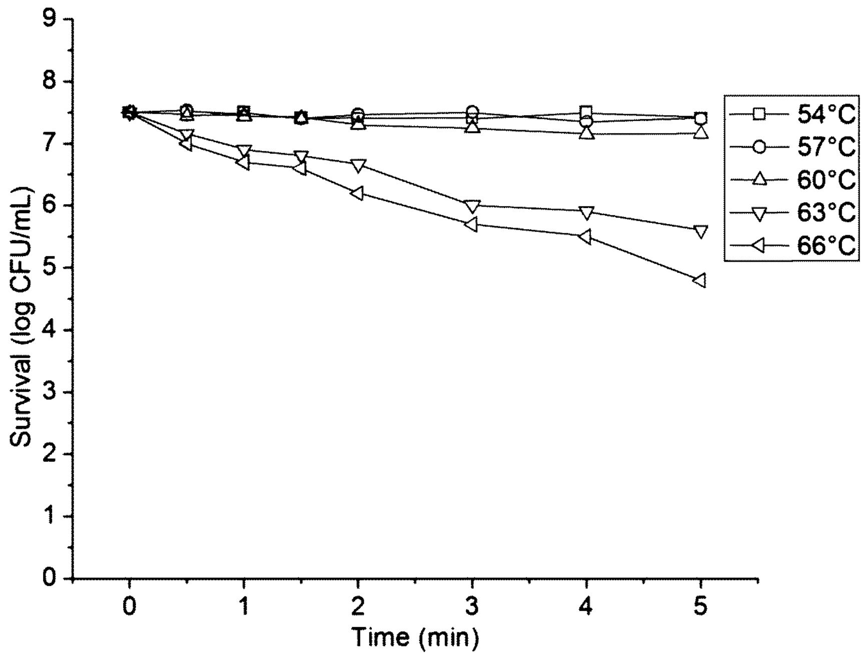
FIG. 3A is a graph showing the thermal stability of *Lactobacillus reuteri* K67 in sodium caseinate solution.

The heat tolerance of the three *Lactobacillus* isolates is shown in FIGS. 3A (K67), 3B (S64) and 3C (LB1). The viability of the three isolates was unchanged at 54° C. for up to 5 min. At 57° C., a decrease of 0.55 log CFU $mL^{-1}$ was obtained for LB1, while the other two isolates showed no decrease in viability up to 5 min. At 60° C., LB1 and K67 experienced decreases of 2.5 log CFU $mL^{-1}$ and 0.35 log CFU $mL^{-1}$, respectively, but no significant change was observed for S64. These results suggest that for each isolate, there is a critical temperature (60° C. for LB1, 63° C. for S64 and K67) above which survival decreases dramatically.

The D-values, or the time required to kill 90% of the cells at various temperatures, of the three different probiotic strains are presented in Table 1. D-values can be used as an indicator of the heat tolerance of microorganisms, such that the greater the D-value, the better the heat tolerance.

TABLE 1

| Temperature | D-value (min) | | |
|---|---|---|---|
| (° C.) | LB1 | K67 | S64 |
| 54 | 333.3 | 212.3 | 333.3 |
| 57 | 12.3 | 62.5 | 88.1 |
| 60 | 3.1 | 18.2 | 44.6 |
| 63 | 2.2 | 3.8 | 8.2 |
| 66 | 1.3 | 2.8 | 3.1 |

Relatively high D-values were found for all three strains at temperatures below 57° C. Among the three isolates, the D-value of S64 was greater than those of LB1 and K67 at all temperatures investigated, indicating that S64 has the best thermal tolerance, while LB1 shows the poorest.

Example 3

Microencapsulation of *Lactobacillus* Isolates

Sodium Caseinate Microencapsulation

Low melting point fat (LMF) was preheated at 50° C. in a water bath to melt all crystals. Vegetable oil or LMF was then added into 100 mL aqueous sodium caseinate (NaCas) solution (10% w/w, 40° C.) with varying ratios of lipid to NaCas (0.25:1.00, 0.50:1.00, and 1.00:1.00 w/w). NaCas solution without vegetable oil or LMF (0:1.00 w/w) was used as a control. The mixtures were coarsely mixed using a blender (Polytron® PT 10-35 GT-D, Kinematica Corporation, Switzerland) at 6000 rpm for 1 min (40° C.) and then recirculated three times through a high pressure homogenizer (Nano DeBEE, B.E.E. International Inc., MA, USA) at 3000 psi (40° C.). The prepared emulsions were left at 0° C. overnight, and *Lactobacillus* cultures (*Lactobacillus reuteri* K67 (K67) or S64 (S64) or *Lactobacillus zeae* LB1 (LB1)) were dispersed into the emulsions and stirred at 100 rpm for 10 min at 0° C. The final mixtures ($10^9$ CFU/g dry coating material) were then spray dried in a laboratory scale spray dryer (ADL 310, Yamato Scientific America Inc., CA, USA), at a constant inlet temperature of 170° C. and outlet temperature of 80° C. and a flow rate of 5 mL/min. Dried powder samples were collected from the base of the cyclone and stored in tightly sealed sterile bottles at 4° C.

Sodium Caseinate-gum Arabic Microencapsulation

Sodium caseinate (NaCas)-gum arabic (GA) complex solutions having ratios of NaCas:GA of 4:0, 3:1, 2:2, 1:3, 0:4 (w/w) (total solid content 10% (w/w)) were prepared in distilled water and stirred overnight at 4° C. The solutions were adjusted to pH 7.0 and pre-heated to 40° C. LMF was then added into the complex solutions at a ratio of 1:1 (w/w). Emulsification, dispersion of *Lactobacillus* cultures into the emulsions and spray drying were carried out as described above.

Example 4

Surface and Internal Microstructure of the Spray Dried Microparticles

Confocal Laser-scanning Microscopy (CLSM)

Microparticles were rehydrated on a glass slide with a drop of triple fluorescent stain (4',6-diamidino-2-phenylindole (DAPI) 0.0005% (w/v), fluorescein isothiocyanate (FITC) 0.0007% (w/v) and 9-diethylamino-5H-benzo[α] phenoxazine-5-one (Nile Red) 0.15% (w/v) in a 100 mM CaCl2 solution). A cover slip was then applied with 4 drops of nail polish in the corners as a spacer to prevent compression of the microparticles. Lipid particles appear orange due to selective staining with Nile Red, bacterial cells appear blue due to selective staining with DAPI and sodium caseinate (NaCas) appears green due to selective staining with FITC. Observations of bacterial cells, protein and lipid were performed with a Carl Zeiss LSM 510 Duo confocal laser-scanning microscope (Gottingen, Germany) using excitation lines at 405, 488 and 532 nm and emission band pass 420-490 nm, 515-550 nm and 575-700 nm for DAPI, FITC and Nile Red respectively.

Results

Figure 2A:
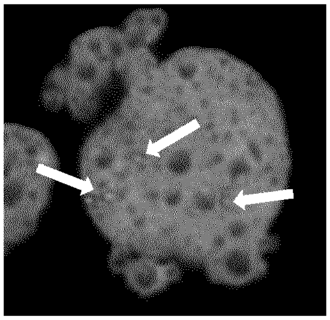
FIG. 2A is a confocal light microscopy image of a spray-dried microparticle according to the embodiment of FIG. 1, in which fat particles appear orange due to selective staining with Nile Red, bacterial cells are indicated by arrows and appear blue due to selective staining with DAPI, and sodium caseinate (NaCas) appears green due to selective staining with FITC.
Figure 2B:
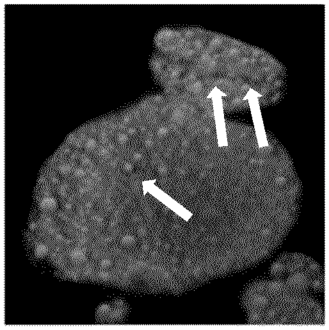
FIG. 2B is a confocal light microscopy image of a spray-dried microparticle similar to the embodiment of FIG. 2A but containing vegetable oil droplets instead of low melting point fat particles.

As seen in FIGS. 2A and 2B, lipid particles (orange) and bacterial cells (blue, indicated by arrows) were dispersed throughout the NaCas matrix (green) with no visible differences between the oil and fat containing samples. With increasing core (lipid) to wall (NaCas) ratio, the density of the oil/fat globules within the particles increased, but the diameter of the oil/fat globules remained constant, possibly because the same process and parameters were applied during the preparation of emulsions and spray drying. Bacterial cells were observed only in the NaCas matrix within the microparticles, and not within the fat particles or oil droplets, reflecting the overall hydrophilic nature of the bacteria surfaces. When mixed with the emulsion, the bacteria are believed to spontaneously move into the hydrophilic phase (NaCas matrix) instead of the hydrophobic phase (oil or fat phase).

Scanning Electron Microscopy (SEM)

The surface morphology of the microparticles was observed with a scanning electron microscope at an accelerating voltage of 20 kV. Prior to recording microscopic observations, carbon sticky tabs were attached to aluminum stubs and the sticky surface was lightly coated with gold for 45 seconds to help reduce charging in the microscope. Small amounts of microparticles were then dusted onto the stubs, spread with a spatula, and the excess particles were blown off with forced air. The stubs were then coated with gold for 2.5 minutes, for a final gold thickness of approximately 8.9 nm.

Results

Figure 2C:
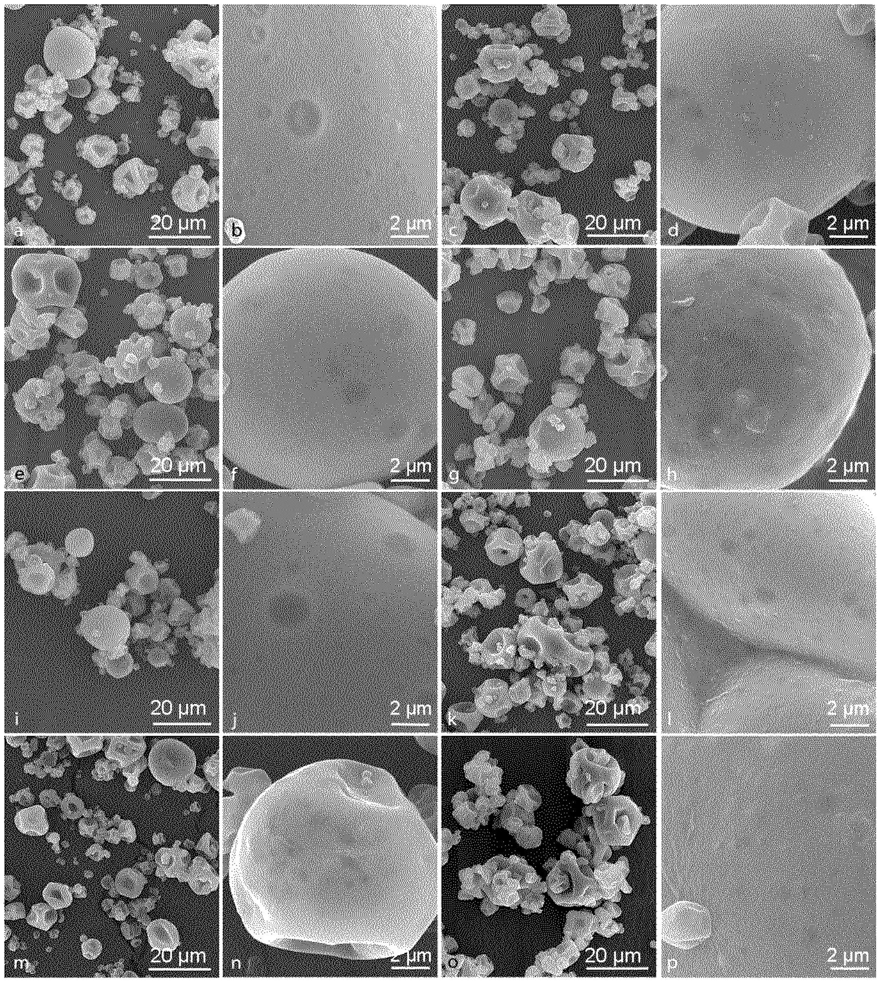
FIG. 2C is a series of scanning electron micrographs of spray-dried microparticles according to the embodiment of FIG. 1 containing vegetable oil and sodium caseinate at ratios (w/w) of 0.25:1 (panels a and b), 0.50:1 (panels c and d), 0.75:1 (panels e and f) or 1:1 (panels g and h) or low melting point fat and sodium caseinate at ratios (w/w) of 0.25:1 (panels i and j), 0.50:1 (panels k and l), 0.75:1 (panels m and n) or 1:1 (panels o and p)

Scanning electron micrographs are presented in FIG. 2C of microparticles produced with varying ratios of oil (panels a to h) or low melting point fat (panels i to p) to sodium caseinate. The diameters of spray dried microparticles were around 15 to 20 μm and no bacteria were observed on the surface of the microparticles. The microparticles containing different lipid core materials (oil or low melting point fat) were similar in appearance, indicating that the lipid used did not affect the morphology of the particles. The shape of the particles varied from irregular to spherical, and the surfaces of the particles were mostly wrinkled with concavities which is believed to be attributed to the shrinkage of the particles caused by rapid evaporation of the water.

Example 5

Survival of Spray Dried Microencapsulated *Lactobacillus* Isolates

Bacterial cell viability of spray dried powders (Example 3) was determined by the standard plate counting method. Spray dried powders (0.5 g) were dispersed in 4.5 mL 0.2M phosphate buffer (pH 7.0) and homogenized for 1 min at 4000 rpm (Polytron® PT 10-35 GT-D, Kinematica Corporation, Switzerland). Enumeration of cells was carried out by plating on MRS agar. Colony forming units (CFU) were enumerated manually after incubation at 37° C. for 24 h.

$$\text{survival rate (\%)} = \frac{CFU/\text{g spray dried powder}}{CFU/\text{g total solid in initial solution prior to spray drying}} \times 100\%$$

Results

Figure 4A:
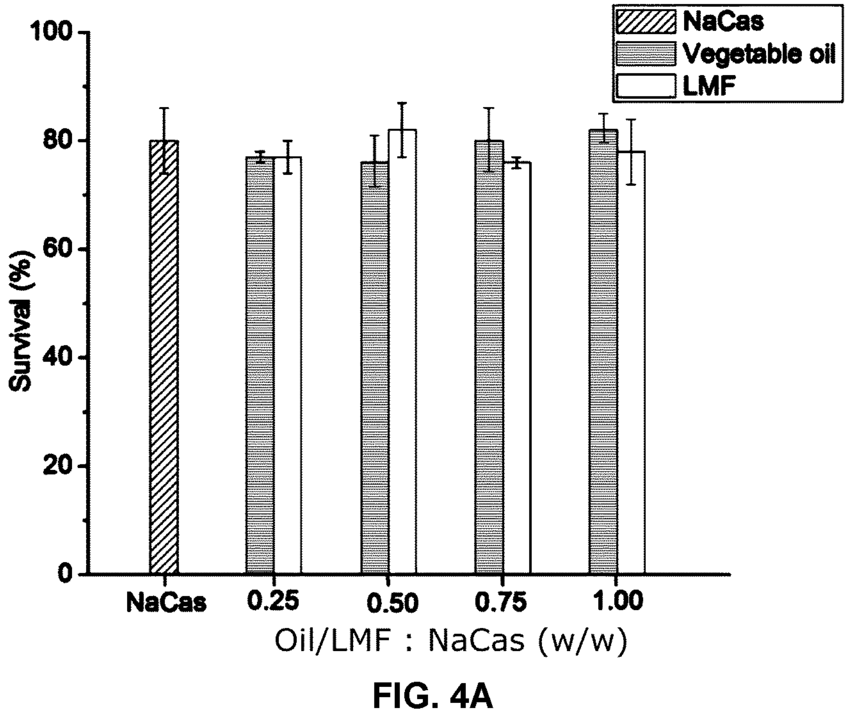
FIG. 4A is a graph showing the survival rate of *Lactobacillus reuteri* K67 encapsulated in spray-dried microparticles including sodium caseinate (NaCas) alone or sodium caseinate including varying amounts of vegetable oil or low melting point fat (LMF)
Figure 4B:
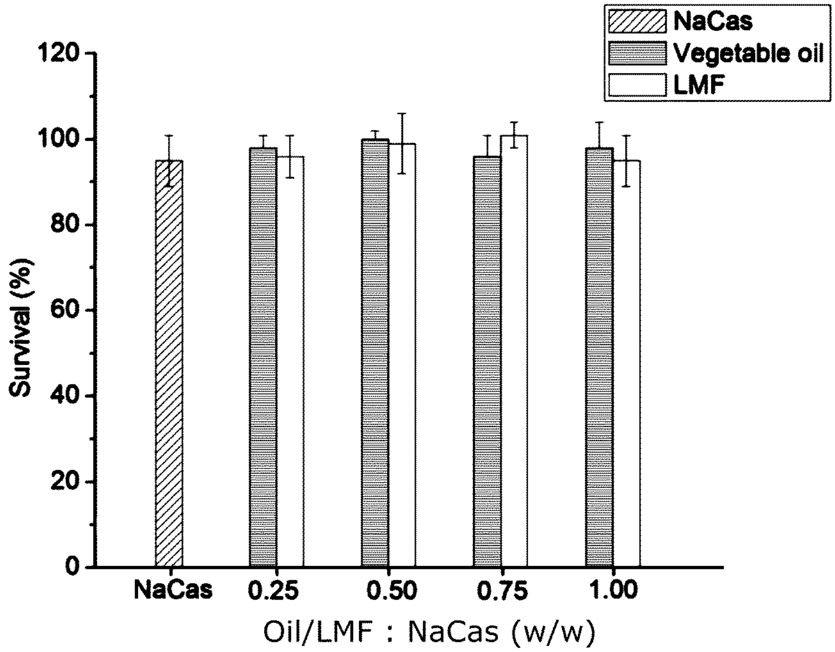
FIG. 4B is a graph showing the survival rate of *Lactobacillus reuteri* S64 encapsulated in spray-dried microparticles including sodium caseinate (NaCas) alone or sodium caseinate including varying amounts of vegetable oil or low melting point fat (LMF)
Figure 4C:
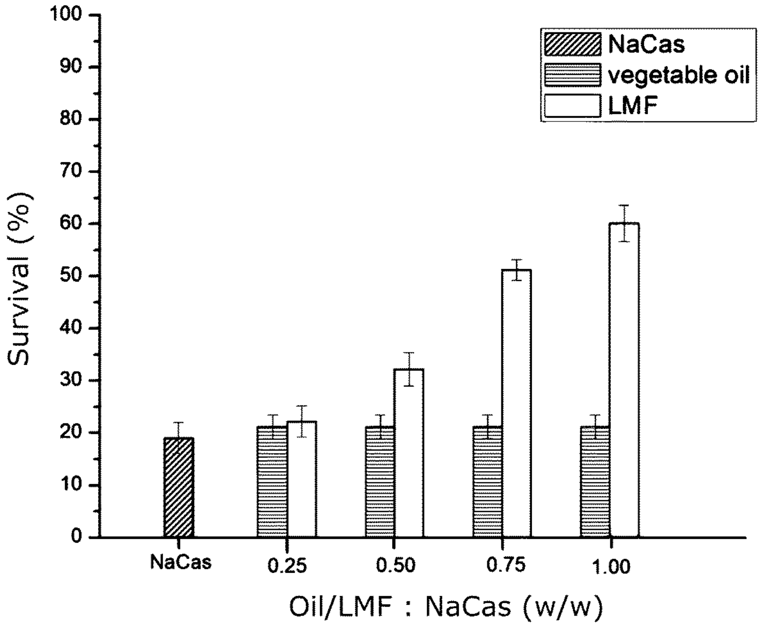
FIG. 4C is a graph showing the survival rate of *Lactobacillus zeae* LB1 encapsulated in spray-dried microparticles including sodium caseinate (NaCas) alone or sodium caseinate including varying amounts of vegetable oil or low melting point fat (LMF)

Among the control samples of the three *Lactobacillus* isolates (i.e. those containing NaCas but no oil or LMF), the highest survival rate (~95%) was obtained with *Lactobacillus reuteri* S64 (S64), as seen in FIG. 4B, which is consistent with the higher thermal tolerance of this isolate as noted in Example 2 above. Addition of either vegetable oil or LMF did not alter the survival rates of *Lactobacillus reuteri* K67 (K67) (FIG. 4A) and S64 (FIG. 4B) after spray drying. However, as seen in FIG. 4C, the survival rate of *Lactobacillus zeae* LB1 (LB1) in the control sample was only about 16%. Among the samples of LB1 containing vegetable oil as core material, the survival rates were almost the same (around 16%), and not significantly different from that in the control sample (p<0.05). In contrast, addition of LMF increased the survival rate of LB1 from 16% to 63% as the LMF to wall ratio increased from 0.25 to 1.00.

Example 6

Salt Tolerance of Microencapsulated *Lactobacillus* Isolates

Fresh cultures and spray dried microparticles prepared as described in Example 3 of *Lactobacillus reuteri* K67 (K67), *Lactobacillus zeae* LB1 (LB1) and *Lactobacillus reuteri* S64 (S64) were plated on MRS agar without NaCl or supplemented with NaCl (5%, w/v). The plates were incubated for up to 3 days under anaerobic conditions and viable numbers were recorded. The survival rate was determined using the following equation:

$$\text{Survival rate (\%)} = \frac{N_s}{N_n}$$

where $N_s$ and $N_n$ represent the survival number grown on MRS agar containing NaCl and MRS agar without NaCl, respectively.

The sensitivity of bacteria to salt was defined as follows:

$$\text{Sensitivity (\%)} = 100(\%) - \text{Survival rate (\%)}$$

Results

Figure 5A:
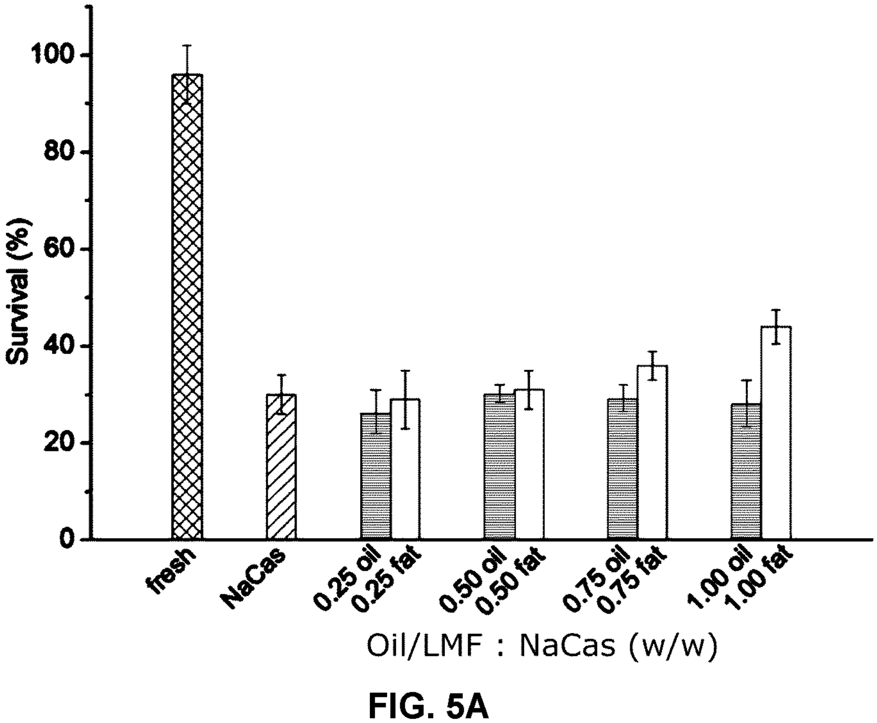
FIG. 5A is a graph showing the survival rate of a fresh culture of *Lactobacillus reuteri* K67, or *Lactobacillus reuteri* K67 encapsulated in spray-dried microparticles including sodium caseinate (NaCas) alone or sodium caseinate including varying amounts of vegetable oil or low melting point fat (LMF), on MRS agar supplemented with 5% NaCl.
Figure 5B:
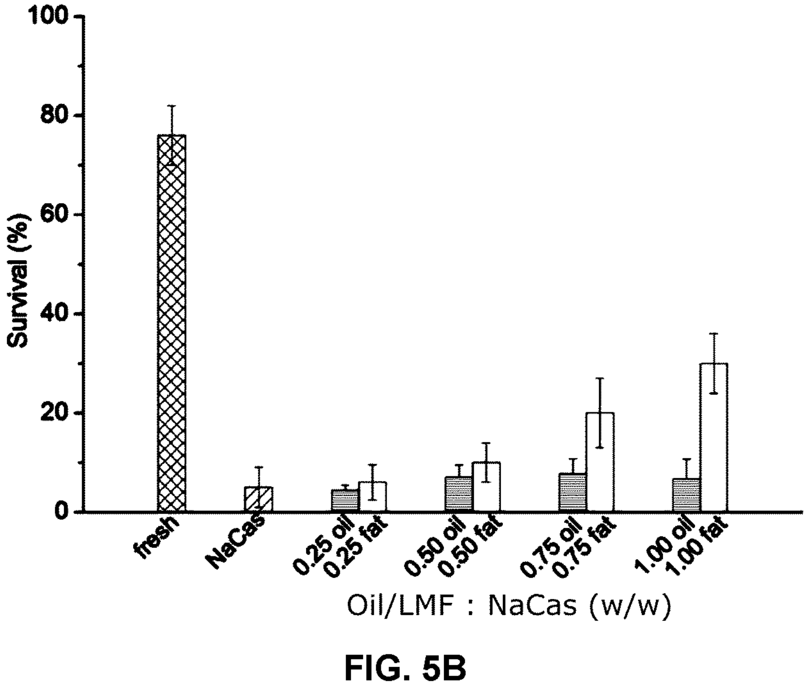
FIG. 5B is a graph showing the survival rate of a fresh culture of *Lactobacillus zeae* LB1, or *Lactobacillus zeae* LB1 encapsulated in spray-dried microparticles including sodium caseinate (NaCas) alone or sodium caseinate including varying amounts of vegetable oil or low melting point fat (LMF), on MRS agar supplemented with 5% NaCl.
Figure 5C:
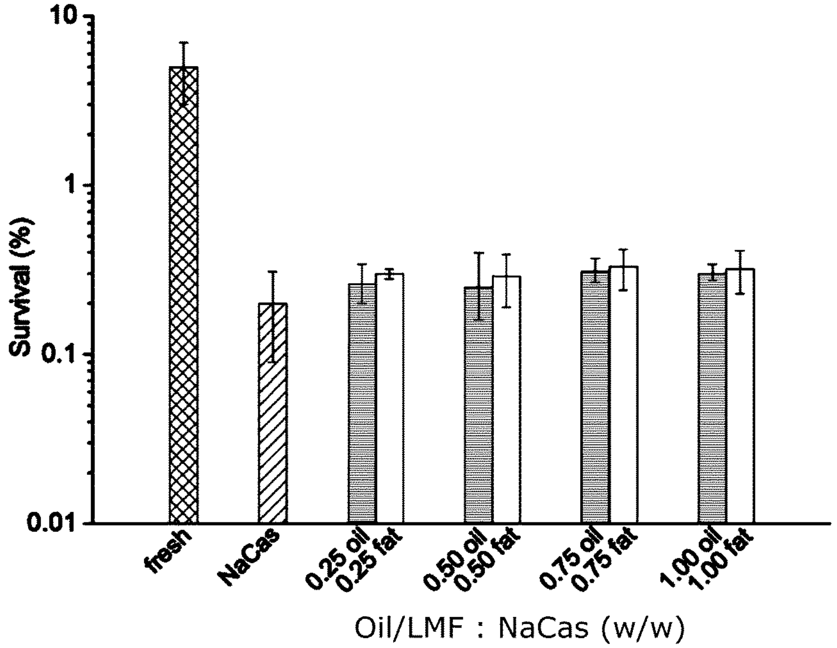
FIG. 5C is a graph showing the survival rate (on a logarithmic scale) of a fresh culture of *Lactobacillus reuteri* S64, or *Lactobacillus reuteri* S64 encapsulated in spray-dried microparticles including sodium caseinate (NaCas) alone or sodium caseinate including varying amounts of vegetable oil or low melting point fat (LMF), on MRS agar supplemented with 5% NaCl.

Fresh cultures of the three isolates exhibited varying degrees of tolerance to salt, with survival rates of 96%, 76%, and 5% for K67, LB1 and S64, respectively, as seen in FIGS. 5A, 5B, and 5C, respectively. The survival rates on NaCl-MRS agar of all spray dried bacterial isolates encapsulated in NaCas without inclusion of oil or LMF were markedly lower than those of the fresh bacterial cultures: 30%, 5%, and 0.2% for K67, LB1 and S64, respectively. For isolates K67 and S64, spray drying induced minimal loss in cell viability (Example 5), but resulted in a significant decrease in salt tolerance. This result suggests that although the bacterial cells survived the spray drying process, some damage to the cell membrane may have occurred, so that the tolerance to salt decreased. In the case of LB1, severe loss of viability was observed after spray drying (Example 5, FIG. 4C), accompanied by further loss of salt tolerance (FIG. 5B), which suggests that the cell damage may be more extensive.

Figure 3B:
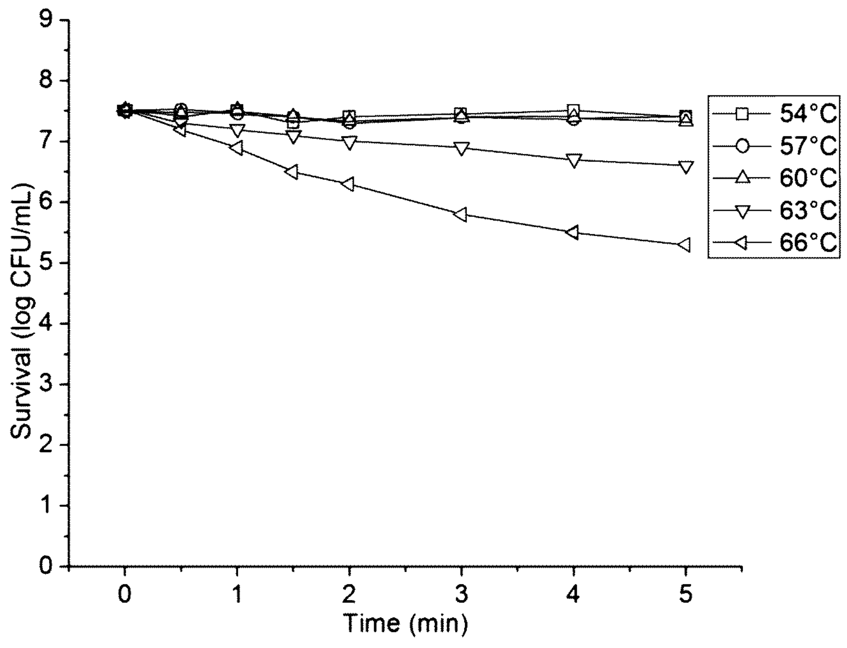
FIG. 3B is a graph showing the thermal stability of *Lactobacillus reuteri* S64 in sodium caseinate solution.
Figure 3C:
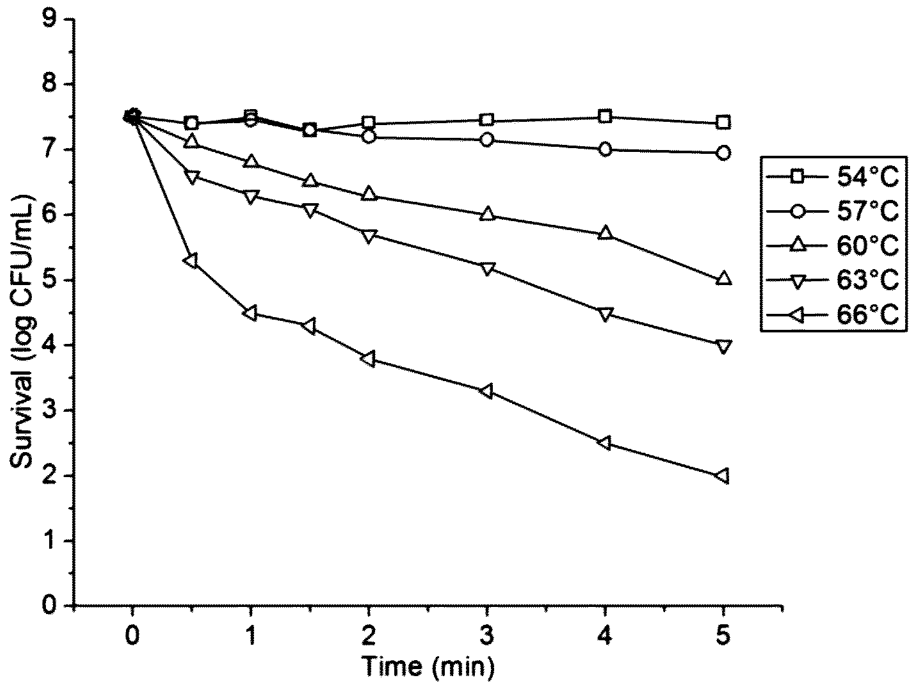
FIG. 3C is a graph showing the thermal stability of *Lactobacillus zeae* LB1 in sodium caseinate solution.

The survival rates on NaCl-supplemented MRS agar of all three isolates microencapsulated with vegetable oil were similar to those in the control NaCas-only microparticles, suggesting that inclusion of oil in the formula did not affect the salt tolerance of bacteria after spray drying. In contrast, significant increases in survival rate on NaCl-supplemented MRS agar were observed for isolates LB1 and K67 in the presence of LMF when the ratio of LMF to wall material reached 1.0 (P<0.05), indicating that the addition of LMF to the microparticles can protect these isolates against damage experienced during spray drying which would have otherwise been expected to further decrease their tolerance to salt. The presence of LMF in microparticles of encapsulated S64 had little effect on the salt tolerance of the relatively thermally tolerant (Example 2, FIG. 3B; Example 5, FIG. 4B) but highly salt intolerant (FIG. 5C) S64 isolate.

Example 7

Survival and Release of Microencapsulated *Lactobacillus zeae* LB1 (LB1) Under Simulated Gastrointestinal Conditions Microparticles (Example 3, 0.1 g) containing *Lactobacillus zeae* LB1 (LB1) encapsulated in a matrix containing varying proportions of sodium caseinate (NaCas) and gum Arabic, and containing low melting point fat in a 1:1 ratio by weight with the encapsulating matrix (Example 3), or free LB1 bacterial cells harvested as described in Example 1 and diluted in sterile 0.85% (w/v) sodium chloride solution to ~$10^9$ CFU/mL (0.1 mL), were added to test tubes containing 9.9 mL of pre-warmed (37° C.) freshly prepared and filter sterilized simulated gastric fluid (SGF) (0.32 wt % pepsin, 0.2 wt % NaCl, adjusted to pH 2.0 with 1M HCl). The samples were vortexed and incubated at 37° C. Samples were removed at 30, 60, 90, and 120 min for bacterial counting, and the pH was then rapidly adjusted to 7.0 with 1M NaOH. Simulated intestinal fluid (SIF) (pancreatin (10 g/L) and bile salts (8 g/L) in phosphate buffer (0.2M, pH=7.0)) (10 mL) was added, and 1 mL aliquots were removed from each sample for bacterial counting after exposure to SIF for a further 1, 2, 3, and 4 h.

For the measurement of protection properties of microparticles, samples (1 mL) were added to 9 mL phosphate buffered saline (PBS) and homogenized for 1 min at 4000 rpm before determination of viable cell numbers. For the measurement of release properties of microparticles, samples (1 mL) were withdrawn without homogenization and directly added into 9 mL PBS for bacterial counting. Enumeration of cells was carried out by plating on MRS agar. Colony forming units (CFU) were enumerated manually after incubation at 37° C. for 24 h.

Results

Figure 6A:
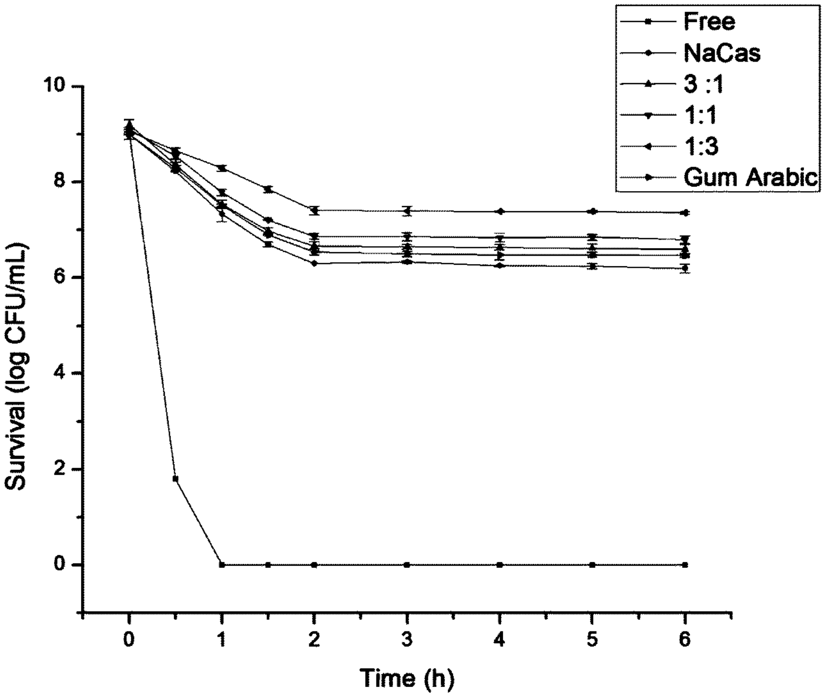
FIG. 6A is a graph showing the survival rate of *Lactobacillus zeae* LB1 encapsulated in spray-dried microparticles including varying proportions of sodium caseinate (NaCas) and gum Arabic in addition to low melting point fat, compared to unencapsulated (free) LB1, when exposed to simulated gastric fluid (1 h-2 h) and simulated intestinal fluid (3 h-6 h)

Survival of encapsulated LB1 during simulated gastrointestinal digestion (2 hours of exposure to SGF, followed by 4 hours of exposure to SIF) is shown in FIG. 6A. Free cells died very quickly and no viable bacterial cells were detected after 1 h in SGF. However, for encapsulated bacteria samples (NaCas with or without gum arabic (GA)), the survival increased significantly. Among these samples, survival rates of bacteria microencapsulated with only NaCas or gum arabic were similar to each other and lower than that of other encapsulated samples. As the gum arabic content in the wall material increased (from a NaCas:GA ratio of 3:1 to 1:3), the survival of encapsulated bacteria increased, with a loss of viability of only 1.2 log over 6 h of test time for the sample having a NaCas:GA ratio of 1:3.

Figure 6B:
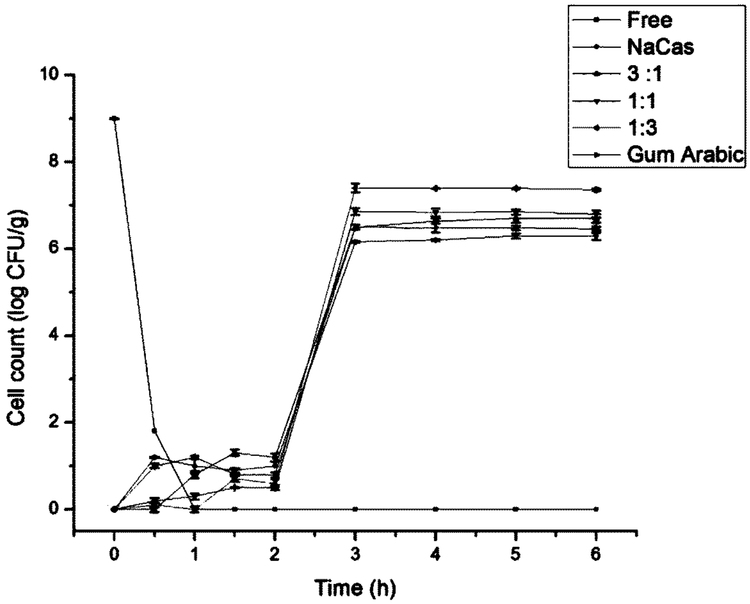
FIG. 6B is a graph showing the release of *Lactobacillus zeae* LB1 from the spray-dried microparticles of FIG. 6A when exposed to simulated gastric fluid (1 h-2 h) and simulated intestinal fluid (3 h-6 h)

Release of encapsulated LB1 during simulated gastrointestinal digestion is shown in FIG. 6B. Free cells died very quickly and no live bacteria were detected after 1 h in SGF. For the encapsulated samples, the number of viable cells released from the microparticles remained constant (0-1 log CFU/g) during the first two hours of exposure to SGF and increased significantly when exposed to SIF. All the viable bacteria in the microparticles were released within 1 h when exposed to SIF.

Example 8

Storage Stability of Microencapsulated *Lactobacillus zeae* LB1 (LB1)

Samples of spray dried microparticles containing *Lactobacillus zeae* LB1 (LB1) encapsulated in a matrix containing varying proportions of sodium caseinate (NaCas) and gum arabic, and containing low melting point fat in a 1:1 ratio by weight with the encapsulating matrix (Example 3) were stored at 4° C. in sealed polyethylene bags placed in sealed glass bottles. Samples were removed at 1 week intervals for determination of viable bacterial count by the standard plate counting method described in Example 5.

Results

Figure 7:
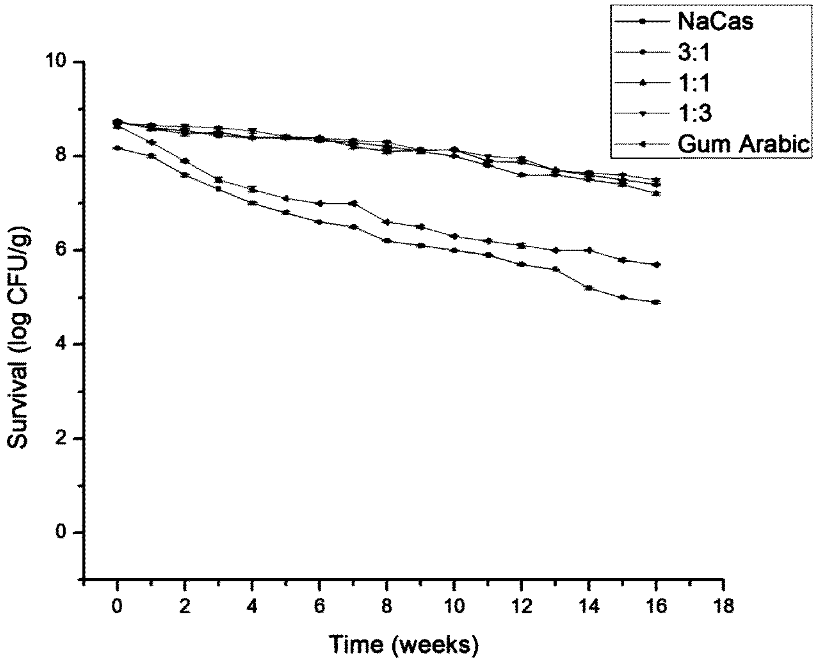
FIG. 7 is a graph showing the survival rate of *Lactobacillus zeae* LB1 from the spray-dried microparticles of FIG. 6A after storage at 4° C. for varying lengths of time.

As seen in FIG. 7, minimal reduction in bacterial count was seen during the first 4 weeks of storage at 4° C. Even after storage for 16 weeks, less than 1 log reduction in viability was observed.

Example 9

Water Content and Water Activity of Spray Dried Microparticles

Spray dried microparticles of *Lactobacillus zeae* LB1 (LB1) were prepared from sodium caseinate (NaCas) alone or mixed with vegetable oil in a 1:1 ratio (w/w) as described in Example 3. Spray drying was carried out at outlet temperatures of 65° C., 70° C., 75° C. or 80° C. A comparison sample of spray dried microparticles of LB1 was prepared from a 1:1 ratio (w/w) of NaCas and LMF at an outlet temperature of 80° C.

Weighing dishes were dried in an oven (105° C.) to a constant weight and then cooled in a desiccator containing silica gel. The weight of the empty dish was recorded (a), approximately 3 g of powder was added, and the dish was weighed again (b). The loaded dish was placed in the oven at 105° C. for 24 h, then cooled to room temperature in a desiccator and weighed again (c). The heating and cooling process was repeated until the weight (c) was constant. The water content was calculated as:

$$\text{Water content} = \frac{(b-c)\times 100\%}{(c-a)}$$

where a is the weight of the empty dish; b is the weight of the dish and the wet powder; and c is the weight of the dish and the dried powder.

The water activity was measured at 25° C. using a water activity meter (Aqualab 4TE, Decagon Devices Inc., USA).

Results

Microparticles spray dried at 80° C. and containing NaCas only were found to have a water content of 6.80% by weight; whereas microparticles spray dried at 80° C. and formulated with a 1:1 ratio of oil:NaCas or LMF:NaCas were found to have a water content of 3.25% by weight and 3.68% by weight, respectively. Assuming that the water is present in the NaCas phase only and is substantially absent from the lipid phase, the water content of the NaCas phase of the microparticles formulated with a 1:1 ratio of oil:NaCas or LMF:NaCas would be 6.78% by weight and 7.67% by weight, respectively. As seen in FIGS. 2A and 2B, the LB1 cells are primarily located in the NaCas phase of the microparticles.

Figure 8A:
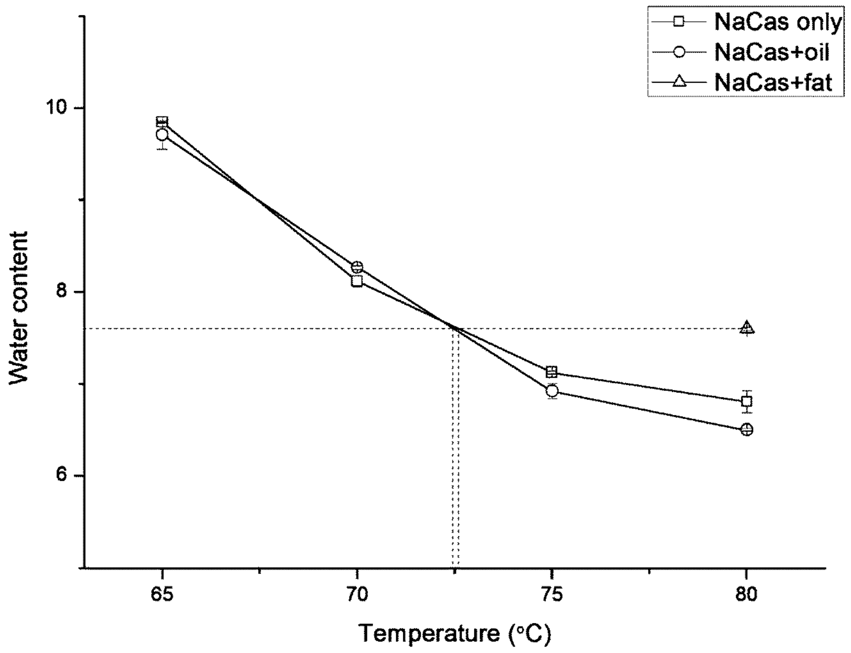
FIG. 8A is a graph showing the effect of outlet temperature on the water content of spray dried microparticles including *Lactobacillus zeae* LB1 and either sodium caseinate (NaCas) alone or a 1:1 ratio (w/w) of sodium caseinate and either vegetable oil or low melting point fat (LMF)
Figure 8B:
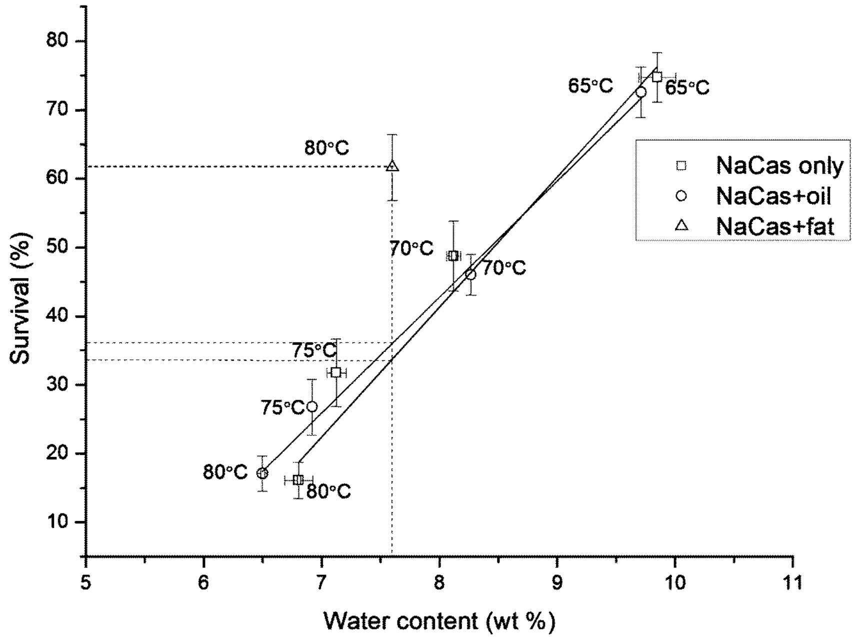
FIG. 8B is a graph showing a plot of the survival rate of *Lactobacillus zeae* LB1 in the spray dried microparticles of FIG. 8A vs. water content.

To determine whether the relatively high water content in the NaCas phase of the 1:1 LMF:NaCas microparticles could have partially contributed to the high survival of bacteria in these microparticles, microparticles having similar water content but containing either NaCas alone or 1:1 oil:NaCas were prepared by spray drying at various outlet temperatures. As seen from the data presented in FIG. 8A, an outlet temperature of about 74° C. would be required to provide microparticles containing either NaCas alone or 1:1 oil:NaCas which would have a water content of about 7.6%, similar to that found in 1:1 LMF:NaCas microparticles spray dried at 80° C. As can be seen from the data presented in FIG. 8B, the interpolated survival rate of LB1 would be similar in microparticles containing either NaCas alone or 1:1 oil:NaCas and having a water content of about 7.6%. However, the interpolated survival rate of LB1 in microparticles containing either NaCas alone or 1:1 oil:NaCas would be much lower than the survival rate observed for LB1 encapsulated in 1:1 LMF:NaCas microparticles spray dried at 80° C. and having a similar water content. This data thus indicates that the water content of the microparticles is not primarily responsible for the improved survival rate of LB1 cells in microparticles containing LMF particles.

Figure 8C:
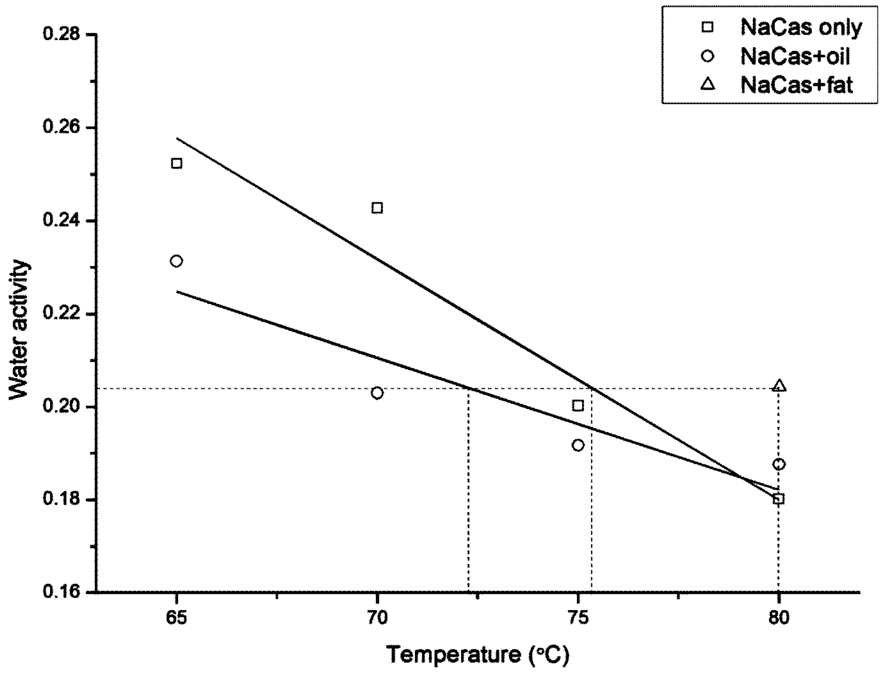
FIG. 8C is a graph showing the effect of outlet temperature on the water activity of the spray dried microparticles of FIG. 8A.
Figure 8D:
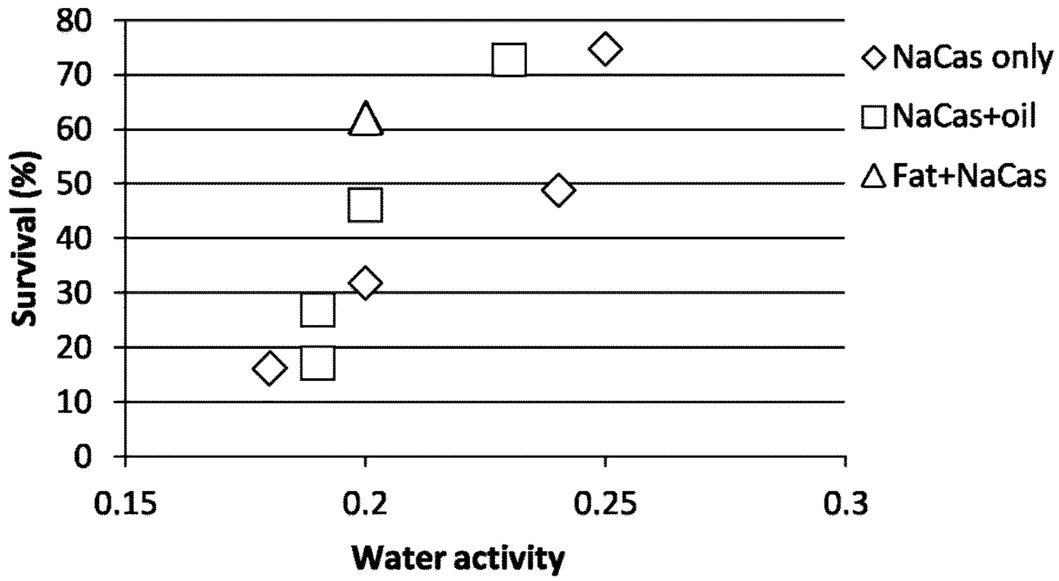
FIG. 8D is a graph showing a plot of the survival rate of *Lactobacillus zeae* LB1 in the spray dried microparticles of FIG. 8A vs. water activity.

Microparticles spray dried at 80° C. and containing NaCas only were found to have a water activity of 0.18; whereas microparticles spray dried at 80° C. and formulated with a 1:1 ratio of oil:NaCas or LMF:NaCas were found to have a water activity of 0.19 and 0.20, respectively. As seen from the data presented in FIG. 8C, the water activity of microparticles formulated with NaCas only and spray dried at an outlet temperature of 75° C. and the water activity of microparticles formulated with 1:1 ratio of oil:NaCas and spray dried at an outlet temperature of 72° C. would be expected to be similar to the water content of microparticles formulated with a 1:1 ratio of LMF:NaCas and spray dried at 80° C. However, as seen from the data presented in FIG. 8D, the survival rate of LB1 in microparticles formulated with a 1:1 ratio of LMF:NaCas and spray dried at 80° C. is improved over the survival rate of LB1 in microparticles having similar water activity but formulated with NaCas only or with a 1:1 ratio of oil:NaCas.

Figure 8E:
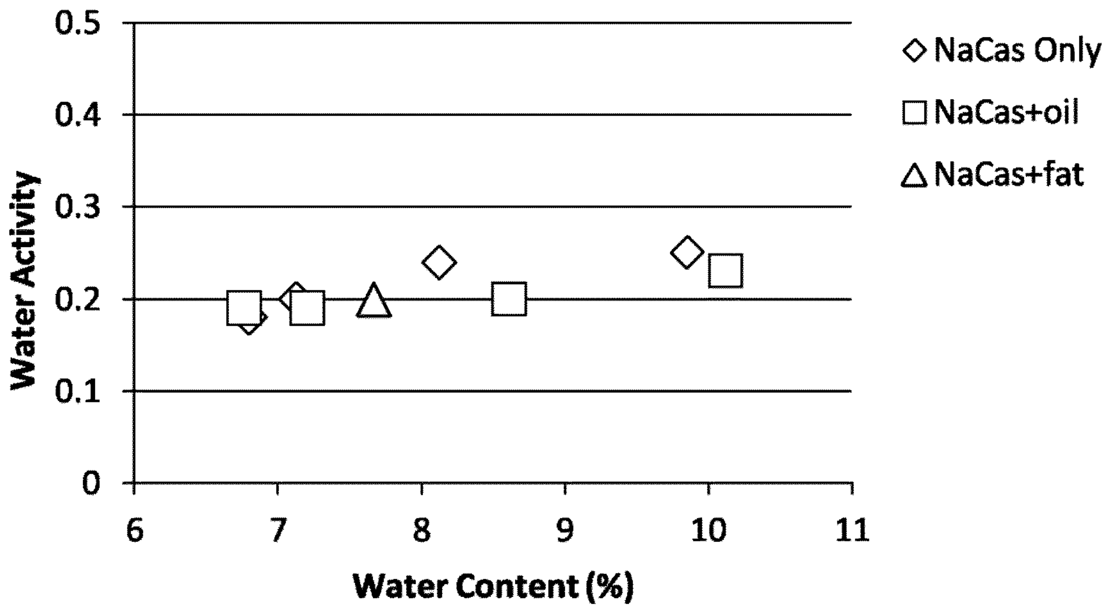
FIG. 8E is a graph showing a plot of the water activity of the spray dried microparticles of FIG. 8A vs. water content.

It is known that a water activity between 0.11 and 0.23 can prevent cell death during storage, while water activity above this range is related to accelerated mortality of probiotics. As seen in FIG. 8E, the water activity of the present microparticles was found to be in the acceptable range for maintenance of the survival of probiotics during storage, over a range of water content values.

Example 10

Thermal Properties of Emulsions Containing LMF or Vegetable Oil

Thermal properties of emulsions containing LMF or vegetable oil in aqueous sodium caseinate (NaCas) solution (10% w/w) (prepared as described in Example 3) were measured using a differential scanning calorimeter (DSC, Auto Q20, TA Instruments, DE, USA). Pure LMF (7 mg) or samples of the emulsion or the non-emulsified 10% (w/w) aqueous sodium caseinate solution (control) (50 mg) were weighed and sealed in aluminum pans and loaded into the DSC. The samples were heated from 0° C. to 80° C. at 1.5° C./min. All measurements were run against an empty pan and heat flow was recorded as a function of temperature.

Results

Figure 9A:
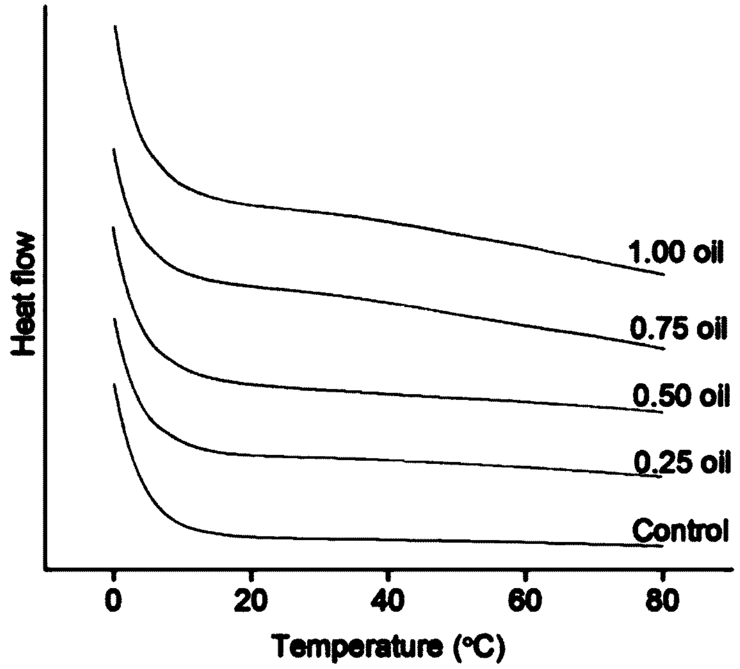
FIG. 9A is a graph showing a series of differential scanning calorimetry (DSC) curves of emulsions of vegetable oil in 10% (w/w) aqueous sodium caseinate (NaCas) solution at various ratios of oil to NaCas; the control is 10% (w/w) aqueous NaCas solution containing no oil.
Figure 9B:
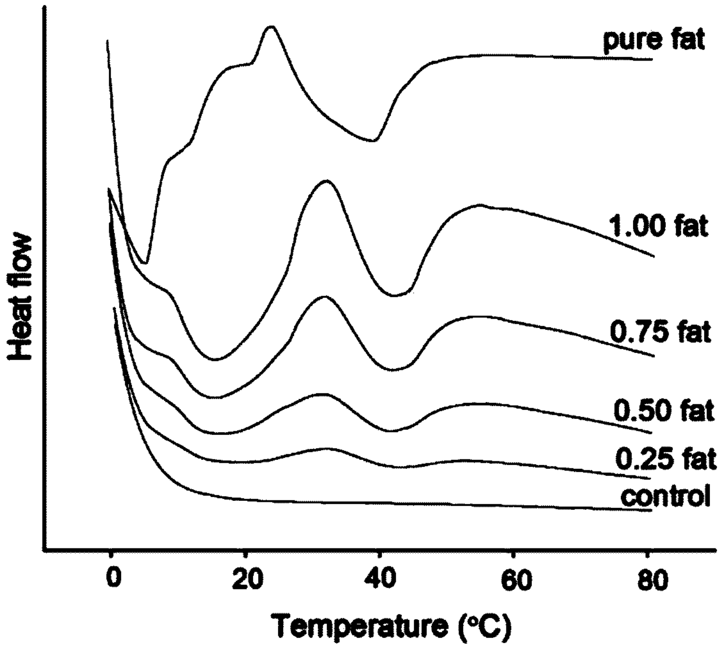
FIG. 9B is a graph showing a series of differential scanning calorimetry (DSC) curves of emulsions of low melting point fat (LMF) in 10% (w/w) aqueous sodium caseinate (NaCas) solution at various ratios of LMF to NaCas; the control is 10% (w/w) aqueous NaCas solution containing no LMF; and pure fat represents unemulsified LMF.

Differential scanning calorimetry (DSC) measures the heat capacity of physical states and the excess heat associated with transitions that can be induced by temperature change. DSC profiles for the vegetable oil or LMF emulsions prepared with different lipid core to sodium caseinate wall ratios are presented in FIGS. 9A and 9B, respectively. Neither endothermic nor exothermic peaks were observed for the control (10% (w/w) aqueous sodium caseinate solution) or emulsions made with vegetable oil in the temperature range from 0° C. to 80° C. (FIG. 9A). As seen in FIG. 9B, however, for the pure LMF sample, there were four peaks in the temperature range of 0° C. to 80° C., at 5.46° C., 12.30° C., 21.13° C. and 40.06° C. These peaks could be associated with the four main fatty acid components with differing chain lengths that constitute the LMF. For the emulsions containing LMF and NaCas at different core to wall ratios, the peak at about 40.06° C. still existed for all samples. However, the first three peaks seen in the pure LMF sample were only observed in samples having a high LMF to NaCas ratio, possibly due to the detection limit of the DSC. With increasing LMF to NaCas ratios from 0.25 to 1.00, the intensity of all peaks increased.

Melting enthalpy (ΔH) represents the energy required to melt the crystal fat present in the samples. The ΔH values of emulsions with different LMF to NaCas ratios are presented in Table 2.

TABLE 2

| | ΔH (J/g) | | |
|---|---|---|---|
| LMF/NaCas (w:w) | peak 1, 2, 3 | peak 4 | Total |
| LMF only | 59.66 | 28.04 | 87.70 |
| 0.25 | 3.53 | 1.61 | 5.14 |
| 0.50 | 7.33 | 3.52 | 10.85 |
| 0.75 | 11.39 | 5.30 | 16.69 |
| 1.00 | 15.42 | 7.25 | 22.67 |

Figure 10:
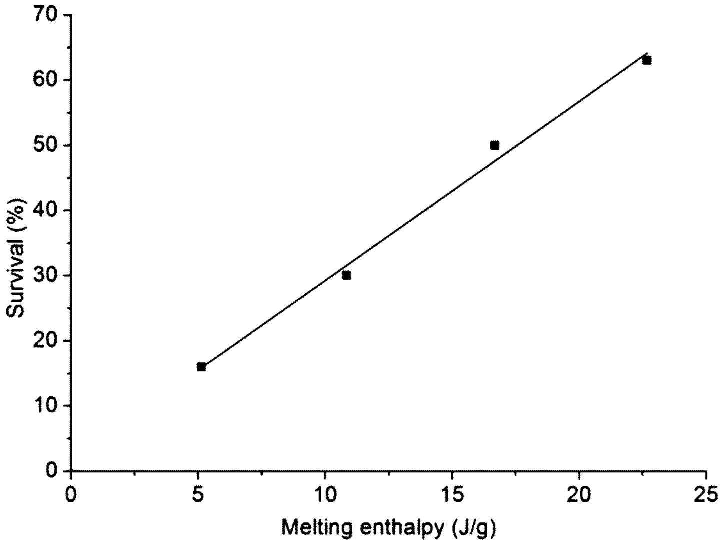
FIG. 10 is a graph of a plot of survival of *Lactobacillus zeae* LB1 encapsulated in spray-dried microparticles including sodium caseinate (NaCas) including varying amounts of low melting point fat (LMF) vs. the melting enthalpy of emulsions of LMF in 10% (w/w) aqueous NaCas solution containing corresponding ratios by weight of LMF to NaCas.

As the LMF to NaCas ratio increased from 0.25 to 1.00, ΔH increased gradually from 3.53 J/g to 15.42 J/g for the first three peaks and from 1.61 J/g to 7.25 J/g for the last peak, respectively. The increased ΔH in the LMF emulsion samples suggested that the addition of LMF would provide the emulsion with endothermic peaks at the temperature around its melting point. The amount of absorbed heat energy increased with increasing LMF:NaCas ratio. For the LMF sample with core to wall ratio of 0.25, the survival rate of LB1 was similar to those of the control and vegetable oil samples. The total melting enthalpy of the LMF/NaCas emulsions with different LMF to NaCas ratios was found to positively correlate with the survival of LB1 after spray drying as shown in FIG. 10.

The embodiments described herein are intended to be illustrative of the present compositions and methods and are not intended to limit the scope of the present invention. Various modifications and changes consistent with the description as a whole and which are readily apparent to the person of skill in the art are intended to be included. The appended claims should not be limited by the specific embodiments set forth in the examples, but should be given the broadest interpretation consistent with the description as a whole.

The invention claimed is:

1. A method of preparing microparticles, the method comprising:

heating a hydrophobic low melting point fat above a melting point thereof to form a liquid melt;

mixing the liquid melt with an aqueous mixture comprising a hydrophilic encapsulating material to form an emulsion;

cooling the emulsion below the melting point of the hydrophobic low melting point fat to form solid particles of the hydrophobic low melting point fat within the emulsion;

dispersing a bioactive material into the cooled emulsion, wherein the bioactive material moves into a hydrophilic phase within the emulsion; and spray drying the cooled emulsion to form the microparticles;

wherein the microparticles comprise the bioactive material dispersed in a matrix of the hydrophilic encapsulating material and solid particles of the hydrophobic low melting point fat dispersed in the matrix of the hydrophilic encapsulating material, and wherein the solid particles of the hydrophobic low melting point fat are substantially separate and distinct from the bioactive material and wherein the solid particles of the hydrophobic low melting point fat protect the bioactive material from heat damage, and wherein the bioactive material is bacteria.

2. The method according to claim 1, wherein the hydrophilic encapsulating material comprises sodium caseinate.

3. The method according to claim 2, wherein the hydrophilic encapsulating material further comprises gum arabic.

4. The method according to claim 1, wherein the hydrophobic low melting point fat has a melting point of about 25° C. to about 60° C.

5. The method according to claim 1, wherein the hydrophobic low melting point fat is selected from shortenings, cocoa butter, margarine, fatty acids, lard, suet, palm oil, fractionated palm oil, hydrogenated oils and mixtures thereof.

6. The method according to claim 1, wherein the bacteria comprises one or more probiotic bacteria.

7. The method according to claim 6, wherein the one or more probiotic bacteria comprise one or more *Lactobacillus* bacteria.

8. Microparticles comprising:

a matrix comprising a hydrophilic encapsulating material;

solid particles of a hydrophobic low melting point fat dispersed in the matrix of the hydrophilic encapsulating material; and a bioactive material dispersed in the matrix of the hydrophilic encapsulating material;

wherein the microparticles are prepared by a method comprising the steps of:

mixing an aqueous mixture of the hydrophilic encapsulating material with a liquid melt of the hydrophobic low melting point fat to form an emulsion;

cooling the emulsion below the melting point of the hydrophobic low melting point fat to form solid particles of the hydrophobic low melting point fat within the emulsion;

dispersing the bioactive material into the cooled emulsion, wherein the bioactive material moves into a hydrophilic phase within the emulsion; and spray drying the cooled emulsion;

wherein the solid particles of the hydrophobic low melting point fat are substantially separate and distinct from the bioactive material in the matrix of the hydrophilic encapsulating material and wherein the solid particles of the hydrophobic low melting point fat protect the bioactive material from heat damage, and wherein the bioactive material is bacteria.

9. The microparticles according to claim 8, wherein the hydrophilic encapsulating material comprises sodium caseinate.

10. The microparticles according to claim 9, wherein the hydrophilic encapsulating material further comprises gum arabic.

11. The microparticles according to claim 9, wherein the hydrophilic low melting point fat has a melting point of about 25° C. to about 60° C.

12. The microparticles according to claim 8, wherein the hydrophobic low melting point fat is selected from shortenings, cocoa butter, margarine, fatty acids, lard, suet, palm oil, fractionated palm oil, hydrogenated oils and mixtures thereof.

13. The microparticles according to claim 8, wherein the bacteria comprises one or more probiotic bacteria.

14. The microparticles according to claim 13, wherein the one or more probiotic bacteria comprise one or more *Lactobacillus* bacteria.

* * * * *